United States Patent [19]

Hughes et al.

[11] Patent Number: 5,475,220
[45] Date of Patent: Dec. 12, 1995

[54] METHOD TO DETERMINE THE PHASE COMPOSITION OF CEMENT

[75] Inventors: Trevor L. Hughes, Cherry Hinton, England; Timothy G. J. Jones, Bethel, Conn.; Philip Fletcher, Aberdeen, Scotland

[73] Assignee: Schlumberger Technology Corporation, Sugar Land, Tex.

[21] Appl. No.: 211,164

[22] PCT Filed: Mar. 17, 1992

[86] PCT No.: PCT/GB92/01714

§ 371 Date: Oct. 6, 1994

§ 102(e) Date: Oct. 6, 1994

[87] PCT Pub. No.: WO93/06461

PCT Pub. Date: Apr. 1, 1993

[30] Foreign Application Priority Data

Sep. 17, 1991 [GB] United Kingdom ............ 9119837

[51] Int. Cl.$^6$ ..................... G01N 21/35; G01N 33/38
[52] U.S. Cl. ..................... 250/339.09; 250/339.08
[58] Field of Search ........... 250/339.09, 339.08, 250/339.11, 339.07

[56] References Cited

U.S. PATENT DOCUMENTS 4,801,445  1/1989  Fukui et al. ............... 424/69

Primary Examiner—Davis L. Willis
Assistant Examiner—Richard Hanig
Attorney, Agent, or Firm—Peter Y. Lee; Wayne I. Kanak

[57] ABSTRACT

A method of analysing the major and/or minor phase composition of a cement comprising a) preparing a calibration model from samples for which the phase composition has been determined and for which infra red spectra, typically Fourier transform infrared spectra, obtained by a diffuse reflectance technique, have been obtained so as to relate differences between spectra of the samples to differences in clinker phase composition of the samples; and b) obtaining the infra red spectrum of a sample of unknown phase composition and determining the phase composition of the sample from the calibration model typically using a multivariate statistical method.

9 Claims, 13 Drawing Sheets

METHOD TO DETERMINE THE PHASE COMPOSITION OF CEMENT

BACKGROUND OF THE INVENTION

1. Field of the Invention

This invention concerns the analysis of samples of neat cement and blends containing a cement component. In particular, the analysis provides a method with which to quantify the various mineral phases in such samples, and is applicable to dry powdered samples of cements such as might be used in the construction industry or oil well operations.

2. Description of the Related Art

Oil-well cementing operations are either "primary", done in the course of drilling a well, or "secondary" or "remedial", intended to remedy deficiencies in primary cementing or alter the well completion for production. During a "primary" cementing process, a cement slurry is pumped down the steel casing and up the annulus between the casing and the surrounding rock formation. The cement slurry must remain sufficiently mobile for the pumping operation to be completed. After it has been placed in the annulus, the cement hardens to form a hydraulic seal in the wellbore, preventing the migration of formation fluids in the annulus. The set cement sheath provides support to the casing string and protects the casing against corrosion by formation fluids. Examples of "secondary" or "remedial" cementing processes are "squeeze" cementing, during which a cement slurry is forced through holes or splits in the casing into voids or a porous rock formation and "plug" cementing, during which a relatively small volume of cement slurry is placed in the wellbore in order to prevent the loss of drilling fluid during the drilling phase or to seal off a depleted zone during the production phase.

The basic ingredient in current cement compositions is portland cement. The raw ingredients of portland cement are lime (CaO), silica ($SiO_2$), alumina ($Al_2O_3$) and iron oxide ($Fe_2O_3$). Lime is obtained from calcareous rock deposits and industrial alkali waste products. Silica, alumina and iron oxide are derived from argillaceous materials such as clays, shales and marls and from artificial sources such as blast furnace slag or fly-ash waste from coal-fired power stations. The diversity of raw materials used to manufacture cements contributes to the wide range of composition of the final products. A pulverised blend of the raw materials is fed into a rotating kiln where temperatures as high as 1500° C. produce a molten mixture; subsequent cooling induces a complex series of reactions to produce the four principal mineral phases: "Alite" which is a tricalcium silicate, $Ca_3SiO_5$ (commonly abbreviated to $C_3S$, which devotes three moles of CAO and one mole of $SiO_2$); "Belite" which is a dicalcium silicate, $Ca_2SiO_4$ ($C_2S$); "Aluminate" which is tricalcium aluminate, $Ca_3Al_2O_6$ ($C_3A$); and "Ferrite" which is tetracalcium aluminoferrite, $Ca_4Al_2Fe_2O_{10}$ ($C_4AF$). These four principal mineral phases leave the kiln as a "clinker" which is subsequently ground with gypsum $CaSO_4.2H_2O$ to produce the finished portland cement product.

The finished portland cement product may contain a variety of sulphate minerals which are produced during the manufacturing process. The added gypsum may dehydrate to bassanite and/or anhydrite during grinding, and it may also react with alkali sulphate to produce syngenite. The concentration and form of the minor sulphate and hydroxide/carbonate components of a cement may have a considerable effect on the slurry performance. For example, the presence of syngenite in oil well cement may cause premature or "false" setting of the slurry.

Specifications for oil-well cements have been established by the American Petroleum Institute (API). There are currently eight classes of API Portland cement, designated Class A through to H which are classified according to the depths to which they are placed, and the temperatures and pressures to which they am exposed. The main chemical criterion for classifying Portland cements is the relative distribution of the four main clinker phases, known as the "potential phase composition". The most widely accepted method of expressing the relative amounts of the principal clinker phases relies upon a series of calculations based on an oxide analysis of the cement sample. This method, based upon various phase equilibria relationships between the cement components, was first introduced in 1929 by R. H. Bogue in his publication, "Calculation of the compounds in portland cement". For each Class of API Portland cement, concentration limits for the Bogue phases, $C_3S$, $C_2S$ $C_3A$ and $C_4AF$ are specified; in addition, limits on the amounts of the alkalis, free CaO, MgO, $SO_3$, insoluble residue and loss on ignition are specified. Other physical parameters which appear in the API specification include the fineness of the cement powder, and the performance of the cement slurry and set cement according to standard tests. The performance tests include measurements of thickening time, compressive strength, expansion and free water.

Whilst the Bogue method of expressing the principal clinker phases in a cement sample has remained the industry standard for many years, it has certain limitations which have lead to the proposal of a "modified Bogue" procedure which may be used to calculate a more realistic "potential phase composition" from a full oxide analysis of a clinker or cement sample.

Infrared spectroscopy has been previously applied to the analysis of cement powders and blends. The use of infrared spectroscopy as a tool for ascertaining the forms of calcium sulphate present (gypsum, hemihydrate, soluble anhydrite, insoluble anhydrite) and whether any hydration (prehydration coupled with carbonation) has occurred or not has been proposed, see II Cemento,1,35–46 (1987). No attempt has been made to deconvolve the infrared spectra with a view to obtaining quantitative analyses of either the minor sulphate and carbonate phases or the principal clinker phases.

Paper WHC-SA-0493-FP prepared for the US Department of Energy, Assistant Secretary for Defense Programs, July 1989, Rebagy, TV and Dodd, DA describes a method to determine the components of cement blends. The proposed method involves the collection of diffuse reflectance FTIR spectra for cement blend samples; the concentration of the components in the blends are determined by using a sequential spectral subtraction program using the spectra of the pure components. Quantitative data pertaining to the analysis of cement, blast furnace slag and fly ash in a 3-component blend and to the analysis of cement, fly ash, attapulgite clay and indian red pottery clay in a 4-component blend are given. The method treats the cement component of the blends as a single component and does not propose a quantification of the individual major and/or minor phases of the cement component of the blend.

SUMMARY OF THE INVENTION

In accordance with one aspect of the present invention, there is provided a method of analysing the phase composition of a cement comprising a) preparing a calibration model by relating measured infrared spectra of samples to the phase composition thereof so as to relate differences between spectra of the samples to differences in phase composition of the samples; and b) obtaining the infra red spectrum of a sample of unknown phase composition and comparing the spectrum with the calibration model so as to determine the phase composition of the sample, characterised in that the model relates the infrared spectra to the composition with regard to more than one phase of the samples and the composition of the sample of unknown phase composition is determined with regard to said more than one phase quantitatively and simultaneously from the infrared spectrum.

The term "phase composition" can relate to the composition of the cement with regard to major and/or minor phases of material forming the cement.

The method can be used to determine the phase composition of a sample of "neat" cement or of a "cement blend", which typically may be in a powdered form. A "cement blend" is a mixture produced by blending a cement component with one or more additional components which commonly include blast furnace slag, fly ash, silica fume, chalk, limestone and various clay materials (eg bentonite). Powdered water-soluble polymer products (eg.hydroxyethyl cellulose) may be also be added to a cement blend. The versatility of the method is such that it may be used for analyte samples which comprise of or contain a cement component of widely varying composition; the cement component may comprise of a clinker or finished cement product of the types used in both the construction and oilfield industries.

Quantification of the phase composition of an analyte sample is achieved by obtaining its infrared spectrum, and by analysing the spectrum using an appropriately designed calibration model which correlates the phase composition and spectra of a series of calibration standards. The infrared spectra used in the method are preferably obtained by Fourier transform infrared (FTIR) spectroscopy and by a diffuse reflectance technique. Quantitative models are normally generated by using spectral data for the mid-infrared region (4000-400 $cm^{-1}$); spectral data for the far-infrared region (below 400 $cm^{-1}$) may be used for some special applications. The technique may be used to obtain an analysis which includes both the major phases of the cement component, i.e. the principal clinker phases and the minor phases such as the sulphates, hydroxide and carbonate phases; such a phase analysis is obtained simultaneously by the processing of a single FTIR spectrum through an appropriate calibration model. Previously proposed techniques for the analysis of the phase composition of cements may involve the use of several analytical techniques eg. XRF or ICP for oxides/Bogue phases and TGA/DTA or XRD for the sulphate phases. A simultaneous analysis using infrared spectroscopy as provided by the present invention has the advantage that it can be performed much more quickly than these methods.

BRIEF DESCRIPTION OF THE DRAWINGS

The present invention will now be described with reference to the accompanying drawings, which comprise.

DETAILED DESCRIPTION OF THE PREFERRED EMBODIMENT

A representative primary sample of the bulk cement or cement blend is taken using appropriate sampling techniques; it is necessary to take a larger primary sample of the bulk when analysing coarse samples such as clinker samples. For the application to clinker samples, the primary sample is crushed using a mechanical grinder (eg. a ball mill grinder) so that all its particles have a diameter less than 10 microns.

An analyte sub-sample of the primary sample is then completely dispersed into a finely ground, nonabsorbing matrix (normally, an alkali halide salt such as potassium bromide) so that the sample concentration in the matrix is 10% by weight. In order to obtain spectra which can be used for quantitative purposes, it is necessary to ensure that the infrared radiation is exposed to a constant quantity of sample particles in the matrix for a fixed period of time. A standardised procedure with which to ensure a constant packing density of the sample/matrix mixture in the diffuse reflectance cell has been developed; the procedure is given below:

a) 0.0450 grams of the analyte sub-sample is thoroughly mixed with 0.4050 grams of potassium bromide.
b) the 10% sample/KBr mixture is completely transferred to a diffuse reflectance cell situated within a compaction cell.
c) a plunger is used to compact the analyte mixture into the cell using a fixed amount of pressure for a fixed period of time.
d) the surface of the compacted analyte mixture is carefully scraped so that it is flat and level with the sides of the diffuse reflectance cell.

Figure 1:
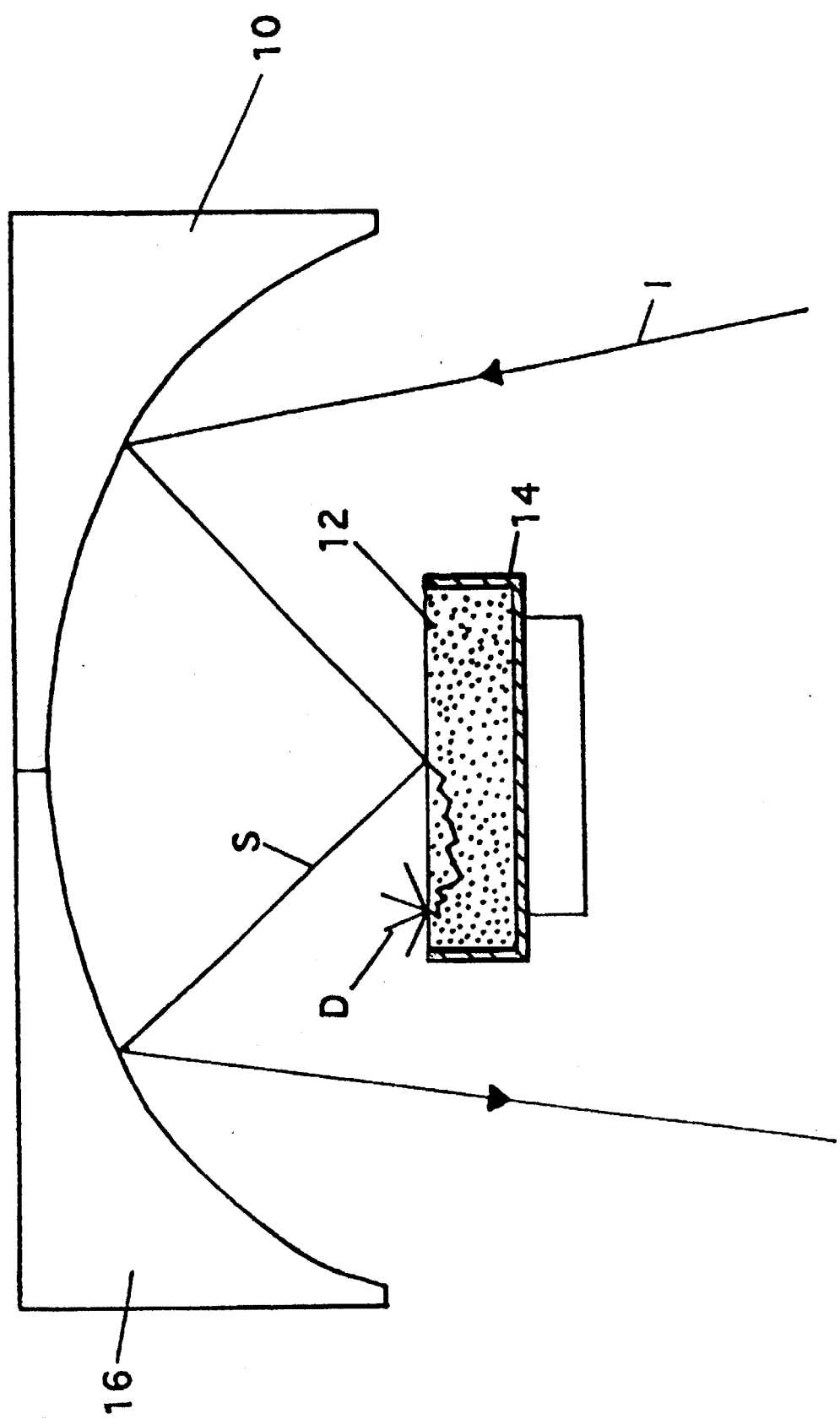
FIG. 1: Schematic diagram of the collection of an infrared spectrum using the diffuse reflectance technique.

The diffuse reflectance cell containing the compacted analyte sample/matrix mixture is inserted into the diffuse reflectance accessory within the infrared spectrometer; the instrumental configuration is shown schematically in FIG. 1. The system for collection of the spectra comprises an IR radiation source (not shown) which directs beam I to an input ellipsoid mirror 10 from where it is reflected onto the sample/KBr mixture 12 in the sample cup 14. The sample cup 14 can be rotated during scanning. The specular S and diffuse D reflectance are directed via an output ellipsoid mirror 16 to a detector (not shown).

The present quantitative method involves the use of spectra which are produced from a fixed number of scans of each sample/matrix mixture; the same number of scans is used to collect the background spectrum of the pure matrix. The accuracy and precision of the method has been improved by the incorporation of a facility for rotating the diffuse reflectance cup during the scanning period.

The design and construction of calibration models will determine the performance of the method. In designing an appropriate calibration model, a number of general rules should be obeyed:

1) the total number of calibration standards used to construct and validate the model must be at least the number of analyte components. In general, as the number of calibration standards is increased, the quality of the model is increased. It is preferred that the number of calibration standards is at least three times the number of analyte components.

2) the compositional variance of the calibration standards should preferably encompass the expected compositional variance of unknown analyte samples; moreover, the spectral variance of the calibration standards should preferably encompass that of the unknowns. Adherence to this rule ensures that subsequent quantitative analysis of unknowns involves interpolation within the spectral and compositional matrices of the model.

3) the characteristics of the mineral phases within the calibration standards should be representative of corresponding phases within the unknowns. This rule is particularly relevant in the design of calibration models with which to quantify the principal clinker phases of a neat cement or of the cement component within a cement blend.

The calibration standards used to construct appropriate quantitative models may comprise of pure mineral phases (e.g. pure tricalcium silicate, $C_3S$, prepared from a mixture of three moles of CaO and one mole of $SiO_2$; pure gypsum, $CaSO_4 \cdot 2H_2O$), mixtures of the pure mineral phases, various clinker and cement samples (both "construction" and "oilfield" types) and various cement blend components such as blast furnace slag, fly ash, clay minerals, silica fume and powdered polymeric additives.

Figure 2:
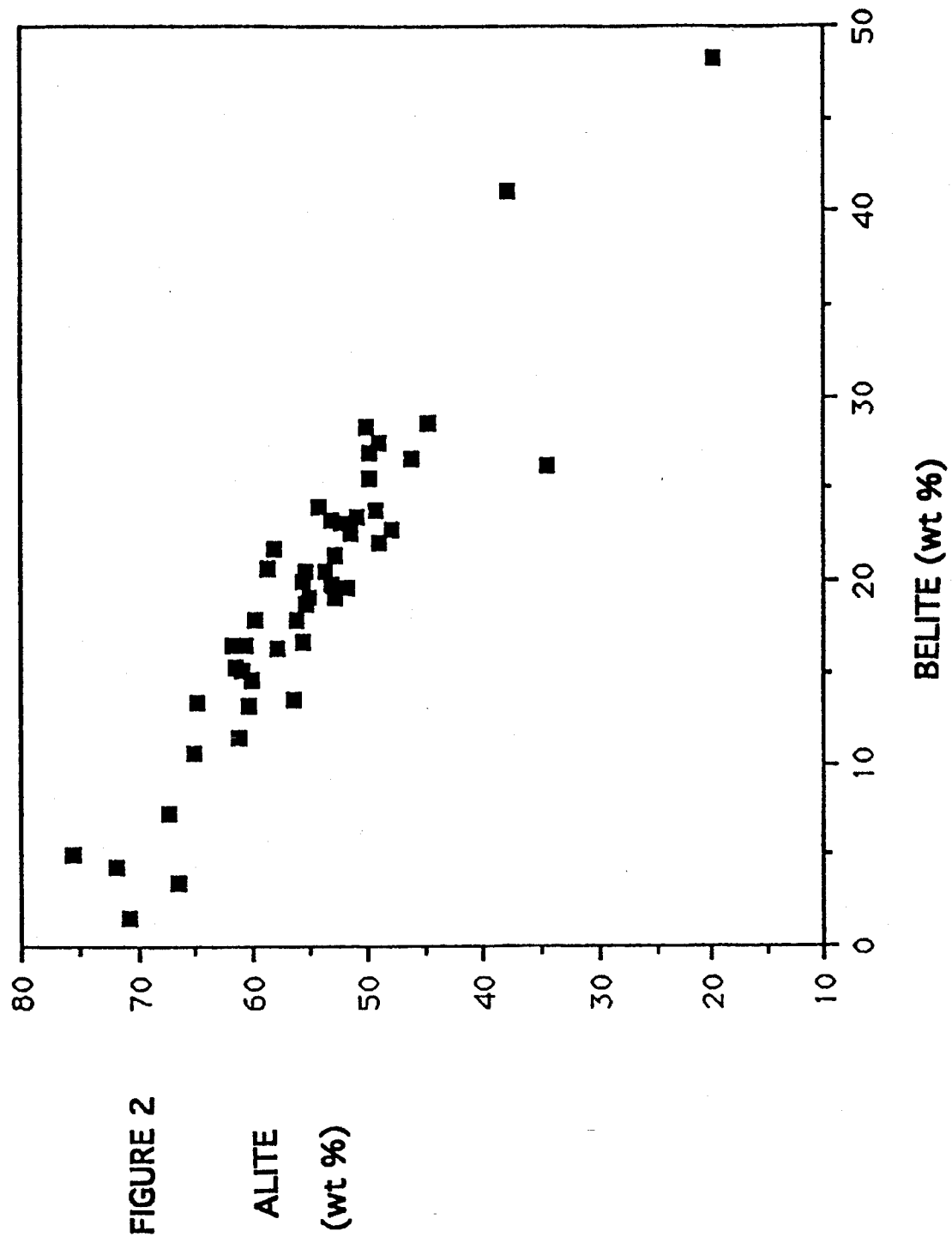
FIG. 2: Plot of alite vs belite content of some typical clinkers and cements.
Figure 3:
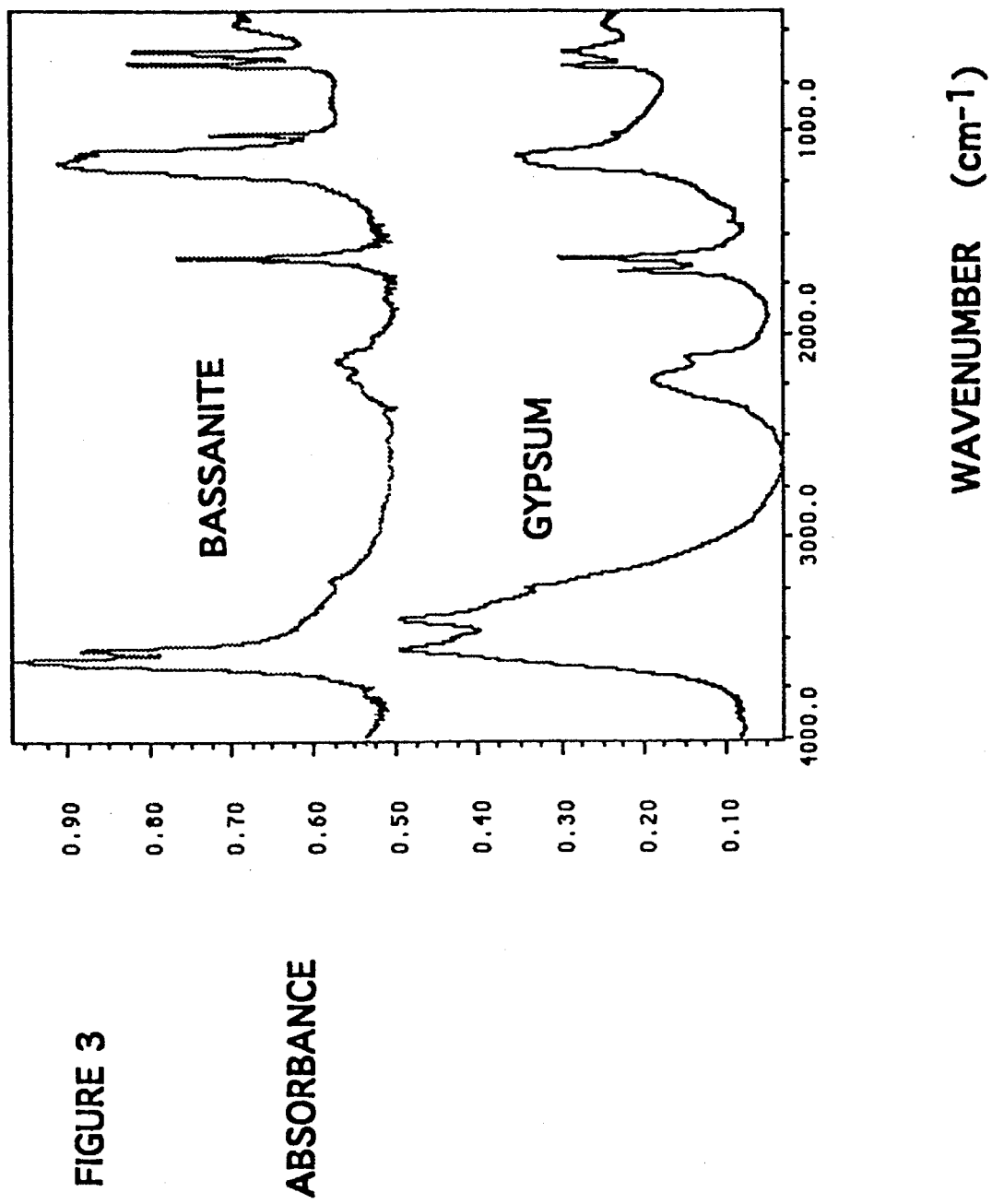
FIG. 3: Infrared spectra of pure gypsum and pure bassanite.

Ideally, the various components of the calibration standards should be varied independently, i.e., there should not be a significant correlation between any two of the components. This is achievable where mixtures of pure mineral phases and/or pure cement blend components are used as calibration standards; in this case, an appropriate series of calibration standards may be designed such that each component is independently varied using a random number generator. However, in many instances, it may be more appropriate to construct a quantitative model based on calibration standards which comprise of or contain "real" clinker and/or cement samples; in this case, it may not be possible to independently vary all of the various mineral phases within the standards. For example, the alite and belite contents of typical clinkers and cements vary dependently as shown for several samples in FIG. 2. If there are significant correlations between the concentration of various components in the calibration standards, then the calibration model will only be reliable for the analysis of samples which also possess the same correlations.

Ideally, the component concentrations for each of the chosen calibration standards should be accurately known. Again, this is achievable for the case where calibration mixtures of pure mineral phases and/or pure cement blend components are used to construct the model. For the case where "real" clinker and/or cement samples are used to construct a calibration model, the compositional data for the standards may be obtained directly using appropriate analytical techniques (eg. light microscopy) or it may be a "potential phase composition" as determined by a transform of the oxide composition according to the Bogue or "modified Bogue" procedures. The oxide composition may be obtained by XRF or ICP analysis of the sample.

A calibration model based on "potential phase composition" data obtained from a Bogue transform of the oxide composition of a series of calibration clinkers/cements may be directly used to determine the appropriate compositional variables specified by the API.

The compositional and spectral data for each of the calibration standards are arranged in the form of data matrices as shown schematically below.

Compositional matrix, C
A B C D E F . . .

$$\begin{pmatrix} 1 \\ 2 \\ 3 \\ 4 \\ 5 \\ 6 \\ . \\ . \\ . \\ n \end{pmatrix} \text{Component concentration values}$$

where A, B . . . are components in the calibration standards

Special matrix, A
$\tilde{V}_1 \tilde{V}_2 \tilde{V}_3 \tilde{V}_4 \tilde{V}_5 \tilde{V}_6 \ldots$ $$\begin{pmatrix} 1 \\ 2 \\ 3 \\ 4 \\ 5 \\ 6 \\ . \\ . \\ . \\ n \end{pmatrix} \text{Absorbance values}$$

where $\tilde{V}_1, \tilde{V}_2 \ldots$ are wavenumbers of the spectra
and 1, 2 . . . n are calibration standards used to construct the model.

The size of the A matrix is determined by the number of calibration standards and the number of data points taken from each of their spectra. Normally, a data resolution of 8 $cm^{-1}$ is used, i.e., absorbance values at 431 equally spaced wavenumbers in the ranges 4000-2400 and 2250-400 $cm^{-1}$ are chosen for each calibration standard (the region 2400-2250 $cm^{-1}$ is omitted because it is sensitive to specific absorbance by carbon dioxide in the atmosphere). For certain applications, it may be necessary to increase the data resolution to <8 $cm^{-1}$. Furthermore, it may be advantageous to exclude spectral data from regions within which the variance of the calibration standards tends to the random variance due to analytical noise.

A number of multivariate statistical techniques may be used to create an appropriate calibration model. For the present method, the partial least squares (PLS) path modelling technique is preferred; other techniques such as principal component regression (PCR) may be appropriate for certain applications.

The basis of the PLS technique has been described in various references, see for example Beebe, RK and Kowalski, BR, *An Introduction to Multivariate Calibration and Analysis,* Anal Chem 59, 1007A–1017A (1987). The first step in the PLS method is to give an equal weighting to the concentration and spectral data by the technique of "autoscaling". The starting point of the PLS calculations is to choose a factor from the concentration matrix, C, and to find the corresponding factors, $t_1$, $t_2$, etc., from the spectral matrix, A. The factor $u_1$ is obtained iteratively, the initial value of $u_1$, $u_1^{(1)}$, is chosen to be any component from the concentration matrix, C, i.e., any normalised column of C. Factor $t_1$ which describes the variation in A due to $u_1$ can now be determined. A weighting factor, w is defined by:

$$w = (u_1^{(1)})^T A$$

where $(u_1^{(1)})^T$ is the transpose of column vector $u_1^{(1)}$. The weighting factor is effectively a correlation coefficient between the concentration of the chosen component and the absorbance at each value of $\tilde{v}$ in the A matrix. The row vector, w, is normalised and the factor, $t_1$, is calculated from:

$$t_1 = A w^T$$

This process extracts a contribution from the scaled values of absorbance at each value of $\tilde{v}$ for each calibration standard. The second estimate of $u_1$ can now be made using a similar cross-correlation process. A weighting vector, r is defined by:

$$r_1 = t_1 C$$

which is effectively the correlation coefficient between factor $t_1$ and the concentration matrix C. The row vector r is normalised and used to generate the second estimate of $u_1$:

$$u_1^{(2)} = C r^T$$

The iteration process continues until $u_1^{(n+1)}$ is not significantly different from $u_1^{(n)}$.

The contribution that factor $t_1$ makes to matrix A is given by the loading vector $b_1$ which is given by:

$$b_1 = t_1^T A$$

The vector $b_1$ is normalised and the resulting product $b_1 t_1$ is the spectral data which can be described by concentration factor $u_1$. The remaining spectral data is:

$$A_1 = A - t_1 b_1$$

and the residue of C is:

$$C_1 = C - \upsilon t_1 r_1$$

where $\upsilon$ is the regression coefficient between $u_1$ and $t_1$. The matrices $A_1$ and $C_1$ are then used to generate the second factors, $u_2$ and $t_2$.

Thus, the PLS technique is used to generate a calibration model by extracting factors t and u from the data matrices A and C. In order to validate the model, the original calibration standards are divided into two groups of standards termed "calibration" and "validation" standards. The "calibration" standards are directly used in the PLS method to generate the calibration model whilst the remaining "validation" standards are used to choose the number of factors such that the fit to the validation samples is optimal. The validation samples are chosen to generally represent the mid regions of the composition range of each component, whilst the calibration samples include the extremes of the concentration matrix. Approximately, one third of the total number of original calibration standards are used in the validation set. A final validation of the calibration model will normally involve the analysis of several independent samples, of known composition; the quantitative compositional data predicted from their spectra is compared to their known composition.

Two examples of the invention are presented. The first example describes the construction and validation of a PLS calibration model specifically designed for the quantitative analysis of the major and minor phases of neat clinker and cement powder samples. This first example is described in some detail and may be used to obtain a rapid and accurate determination of the phase composition of both construction and oilfield type clinker and finished portland cements. The second example describes the validation of a calibration model designed for the determination of the phase composition of cement/silica fume blends.

35 calibration standards were chosen for the construction of the calibration model; 26 of the samples are oilfield type cements, 7 are construction type cements and 2 are construction type clinker samples. The use of both oil field and construction type cements increases the variance within both the concentration and spectral matrices.

The mid-infrared spectrum of each of the calibration standards was collected using the procedures described above. The spectral matrix, A, was constructed using 431 equally spaced absorbance data points from the 4000-2400 and 2250-400 wavenumber regions of each of the 35 spectra.

The concentration matrix, C, contains the concentration of eight components within each of the calibration standards. The eight components are Alite, Belite, Aluminate, Ferrite, free lime, alkali sulphate, gypsum and bassanite. Values of the concentration of the four principal clinker phases were calculated from accurate oxide analyses, typically obtained by XRF or ICP, for each calibration standard using the conventional Bogue calculation. The alkali metal oxides, $Na_2O$ and $K_2O$, were assumed to be entirely associated with the "alkali sulphate" phase also determined from oxide analysis whilst the residual sulphur trioxide, $SO_3$ was assumed to be associated with the calcium sulphates.

Figure 4:
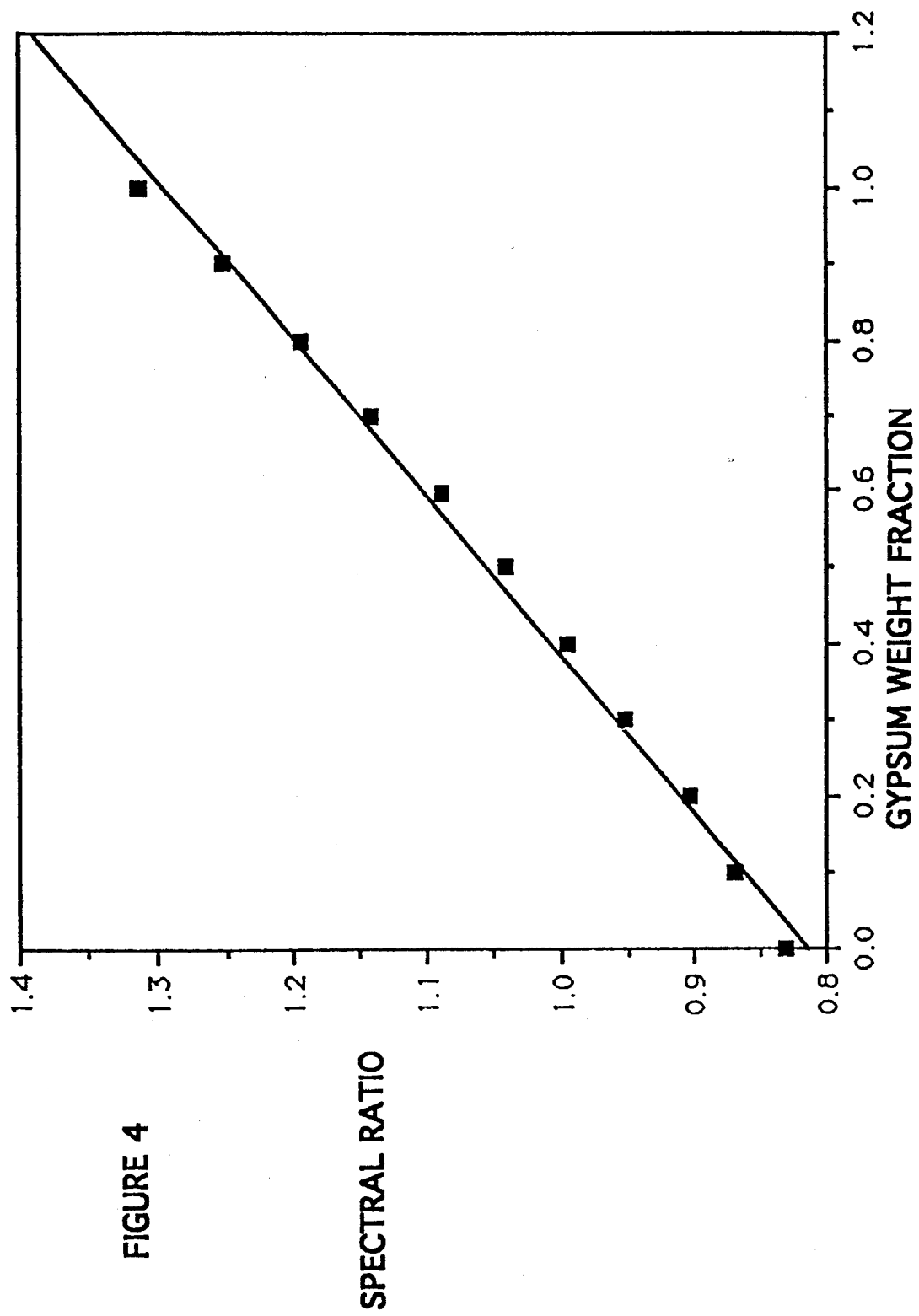
FIG. 4: Plot of relationship between spectral ratio and gypsum/bassanite ratio for gypsum/bassanite mixtures.
Figure 5:
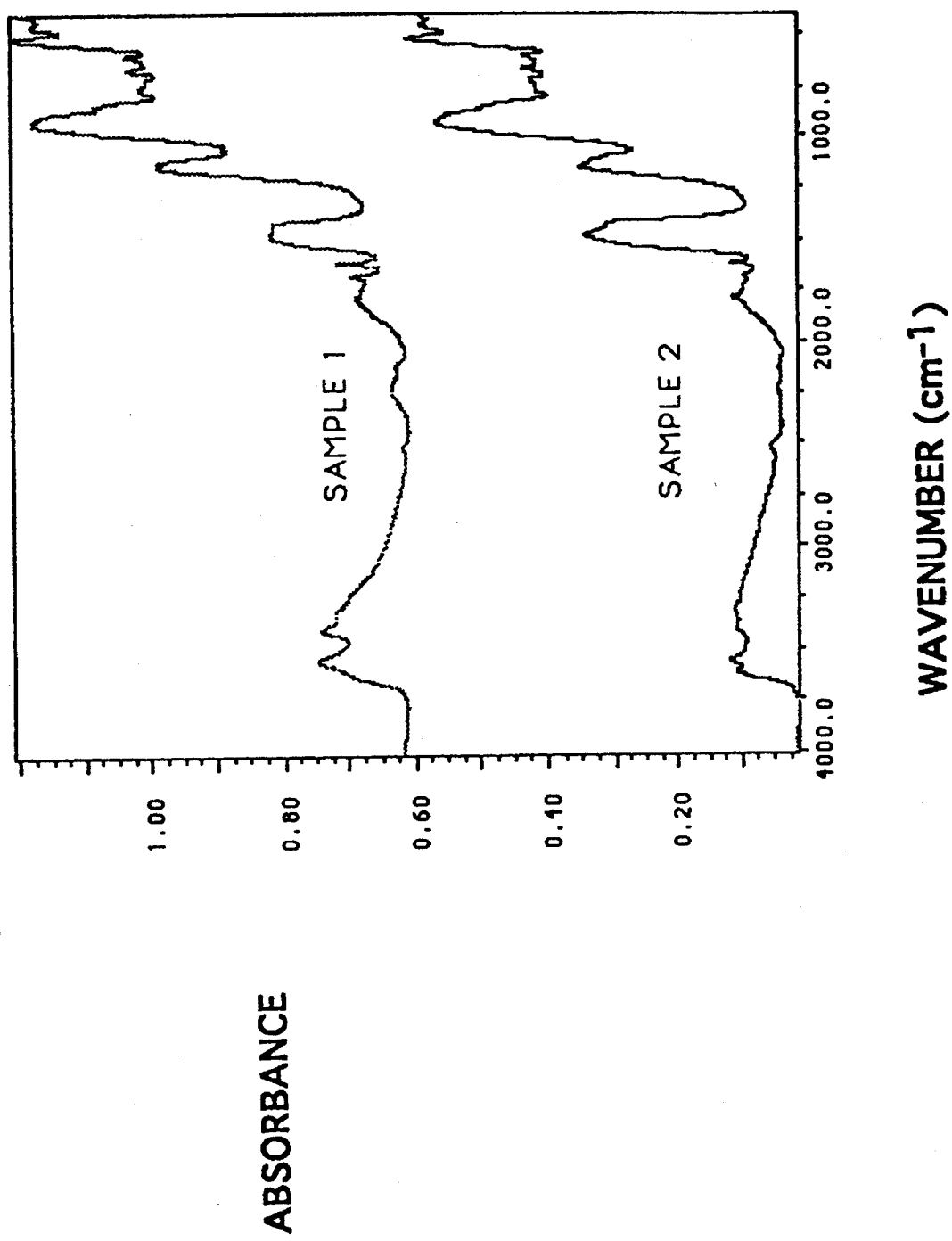
FIG. 5: Infrared spectra of two calibration standards.
Figure 6:
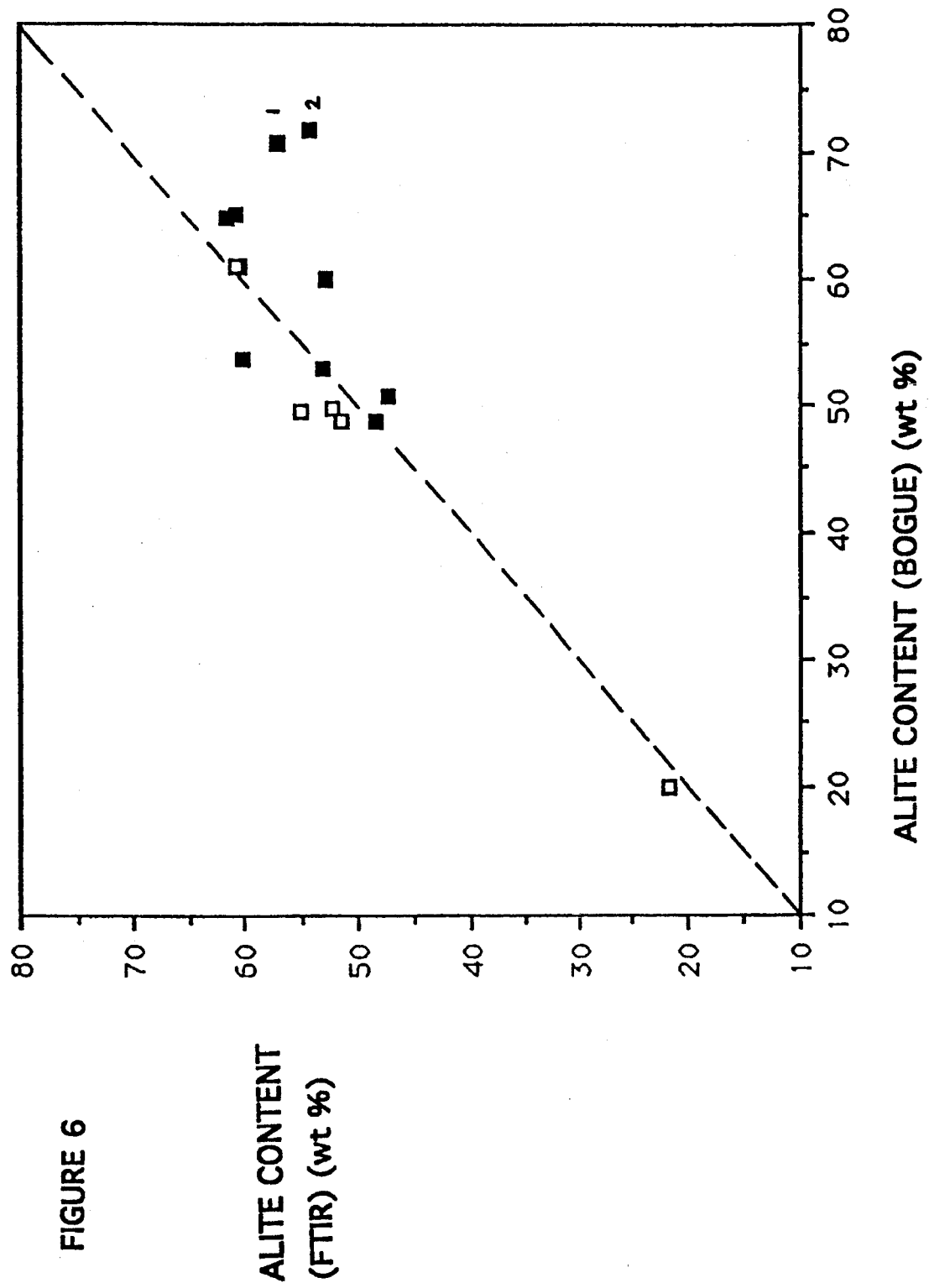
FIG. 6: Prediction of alite content from FTIR spectra: validation samples.

The calcium sulphate content of each calibration standard was divided into gypsum, $CaSO_4 \cdot 2H_2O$ and bassanite, $CaSO_4 \cdot \tfrac{1}{2}H_2O$ contents using a technique which involves a detailed examination of the spectra. The mid infrared spectra of the pure components, gypsum and bassanite are shown in FIG. 4. For a series of gypsum/bassanite mixtures, absorbance values at the wavenumbers, $\tilde{v}_1$ (3554 cm$^{-1}$) and $\tilde{v}_2$ (3604 cm$^{-1}$) were noted; as shown in FIG. 5, the ratio of the absorbances, $\tilde{v}_1 / \tilde{v}_2$ varies linearly (correlation coefficient= 0.9975) with the weight fraction of gypsum in the mixtures. The FTIR spectra of two of the calibration standards are shown in FIG. 6; a comparison with the spectra in FIG. 4 indicates that whilst the sulphate in sample 1 is dominated by gypsum, that of sample 2 is dominated by bassanite. The linear relationship shown in FIG. 5 was assumed to be applicable to the spectra of the calibration samples. Having made this assumption, values of the ratio $A_{\tilde{v}}1 / A_{\tilde{v}}2$ from the spectra and total calcium sulphate contents from the oxides data were used to calculate the gypsum and bassanite contents of each calibration sample. It is important to note that this method of calculating gypsum and bassanite contents may not be applicable to cements which contain significant quantifies of other minor sulphates such as syngenite and anhydrite. Alternative spectral examination methods are employed in constructing models which are designed for the quantification of syngenite and anhydrite (for example, absorbances at the wavenumbers, 3321 and 1190 cm$^{-1}$ are particularly important for the quantification of syngenite). The concentration of "free lime" in each of the calibration standards was determined by the standard ASTM titration method. Alternatively the concentration of calcium hydroxide and calcium carbonate can replace "free lime" or components in the model.

Figure 7:
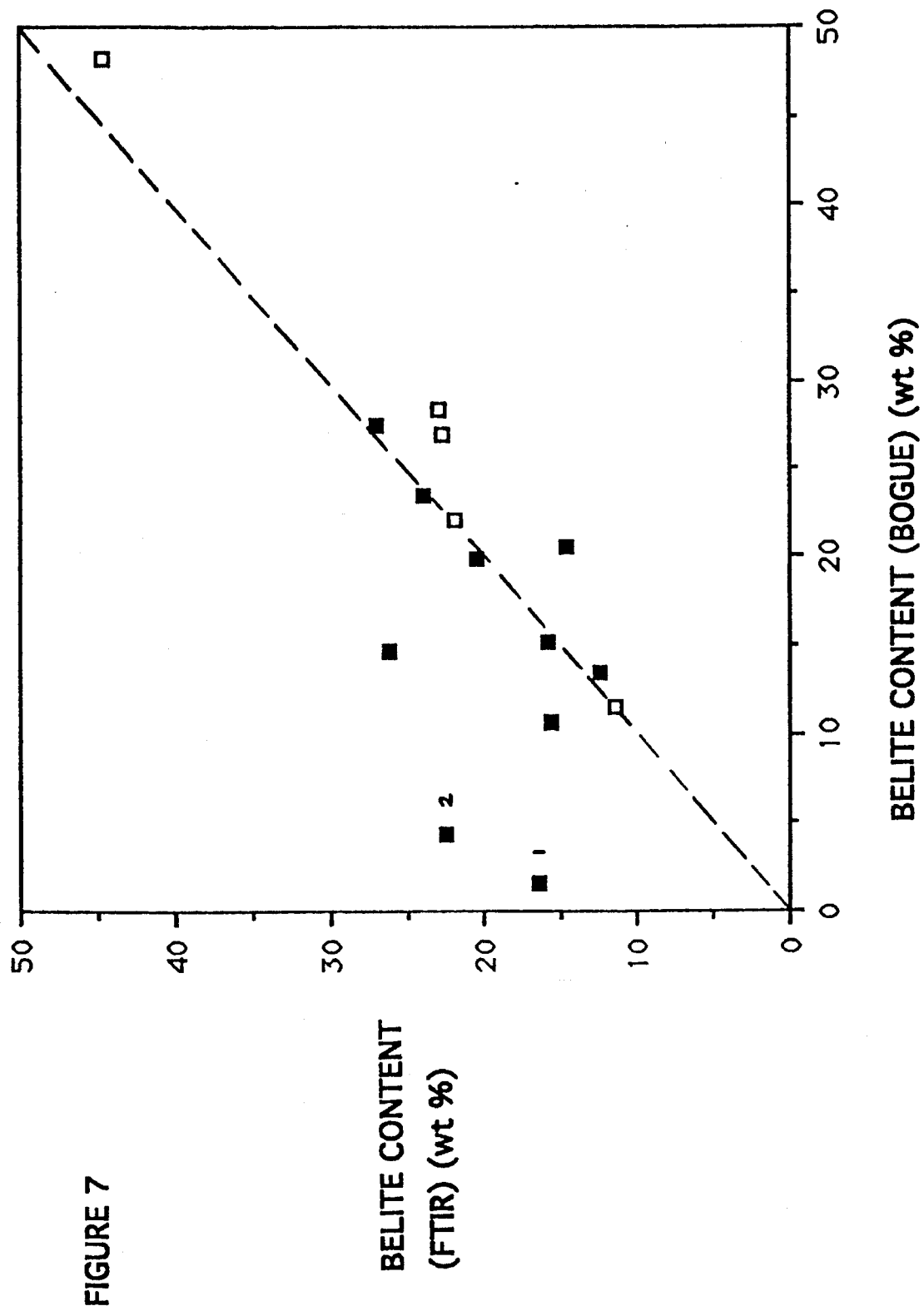
FIG. 7: Prediction of belite content from FTIR spectra: validation samples.
Figure 8:
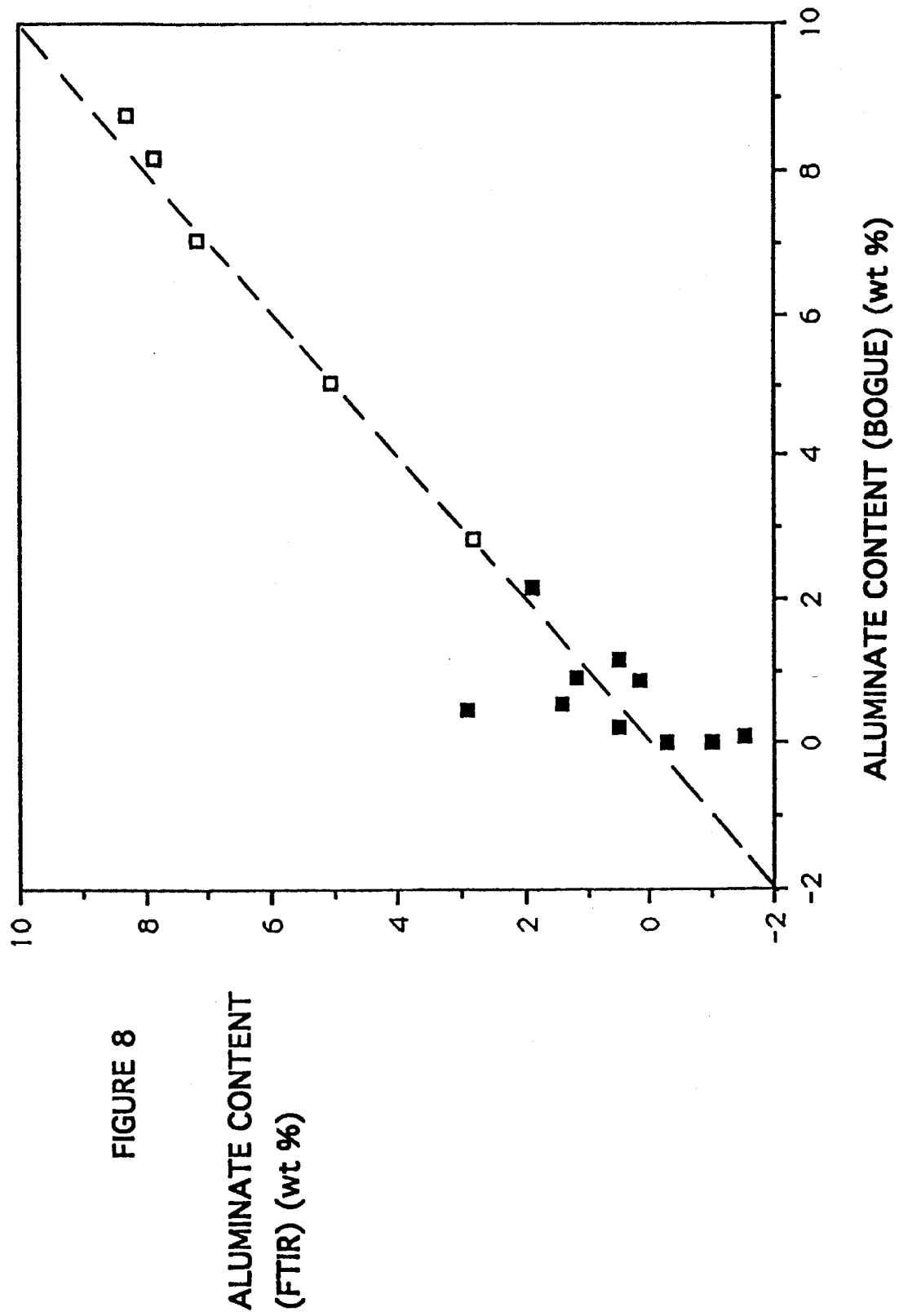
FIG. 8: Prediction of aluminate content from FTIR spectra: validation samples.
Figure 9:
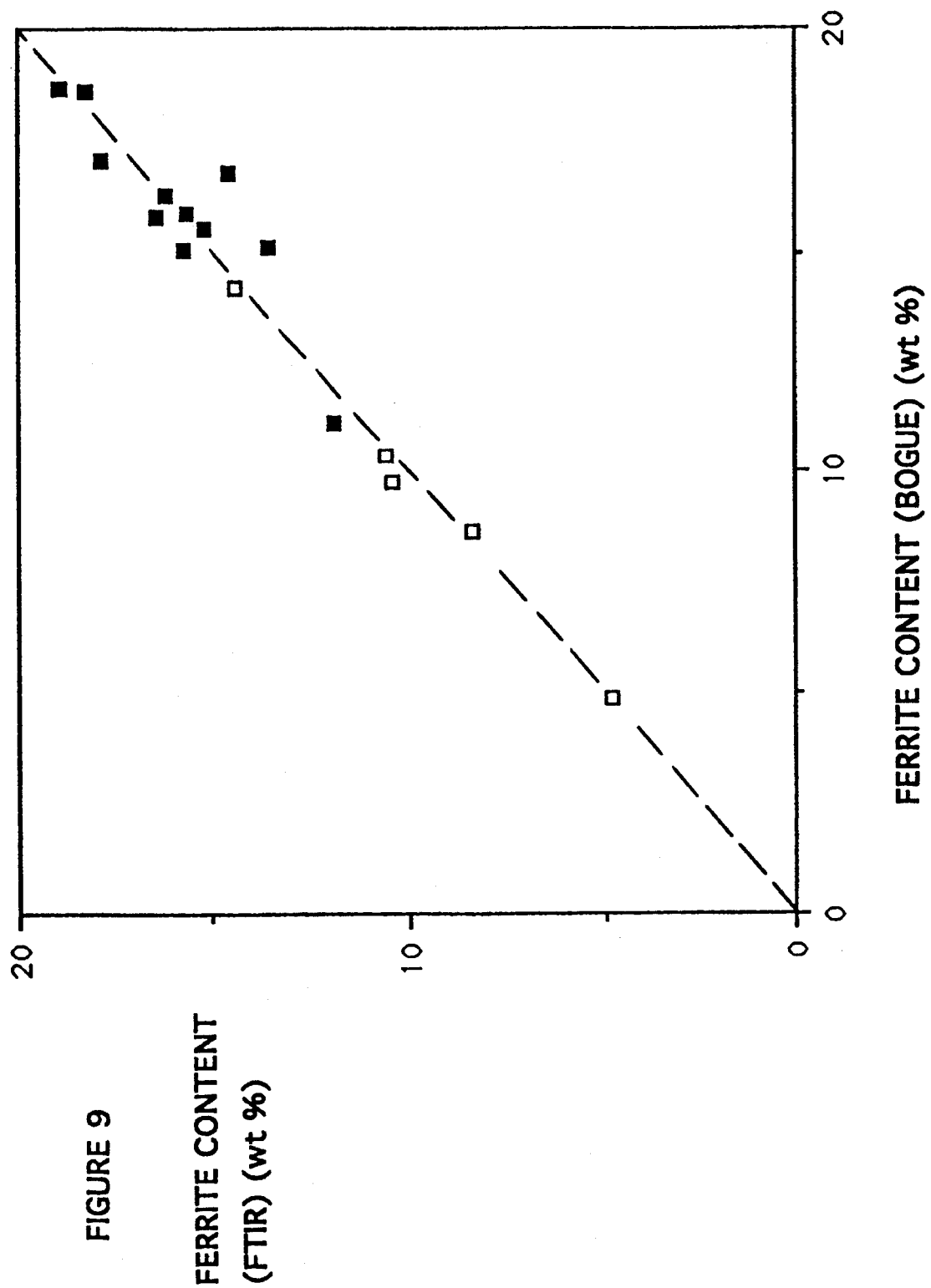
FIG. 9: Prediction of ferrite content from FTIR spectra: validation samples.
Figure 10:
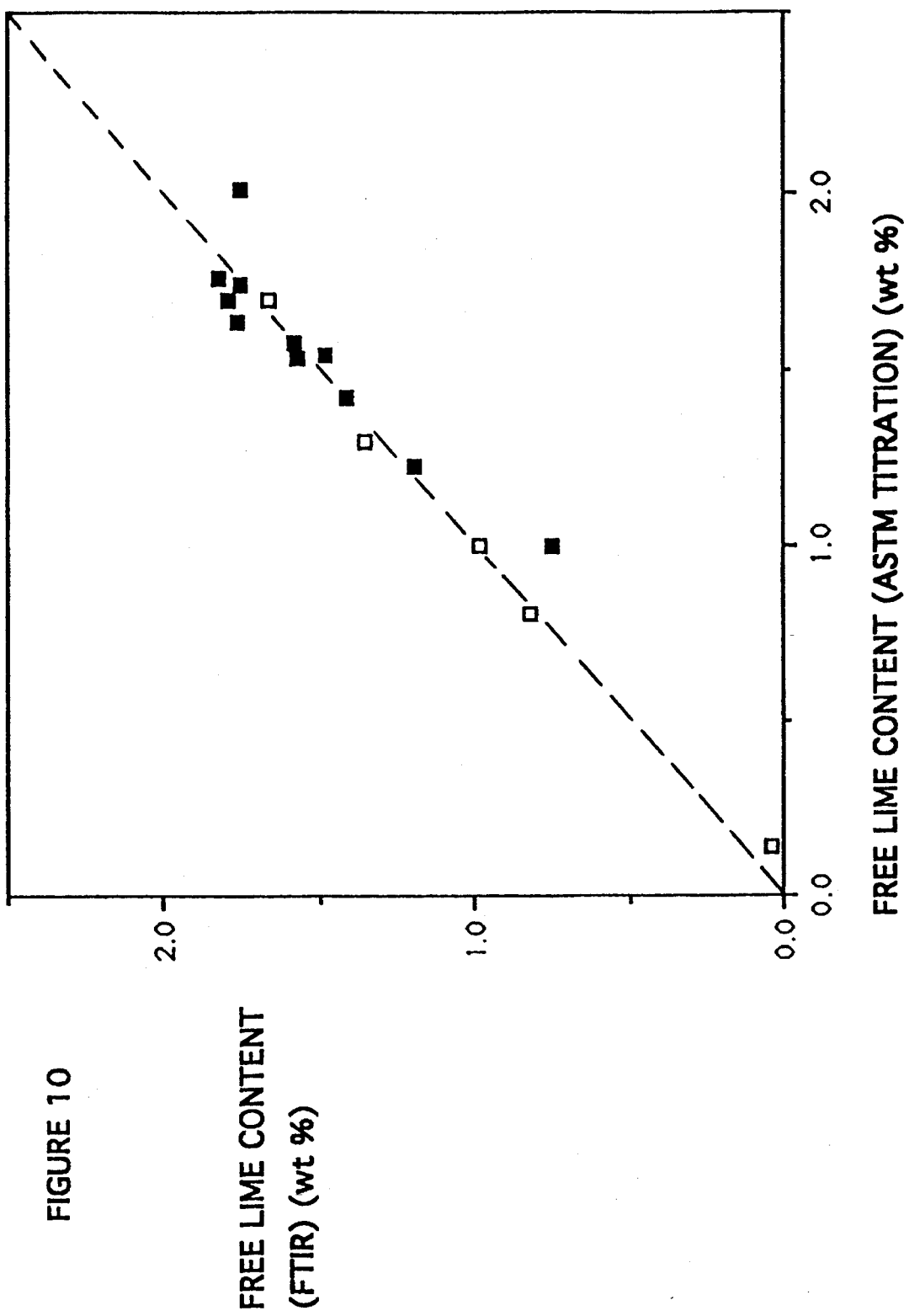
FIG. 10: Prediction of free lime content from FTIR spectra: validation samples.
Figure 11:
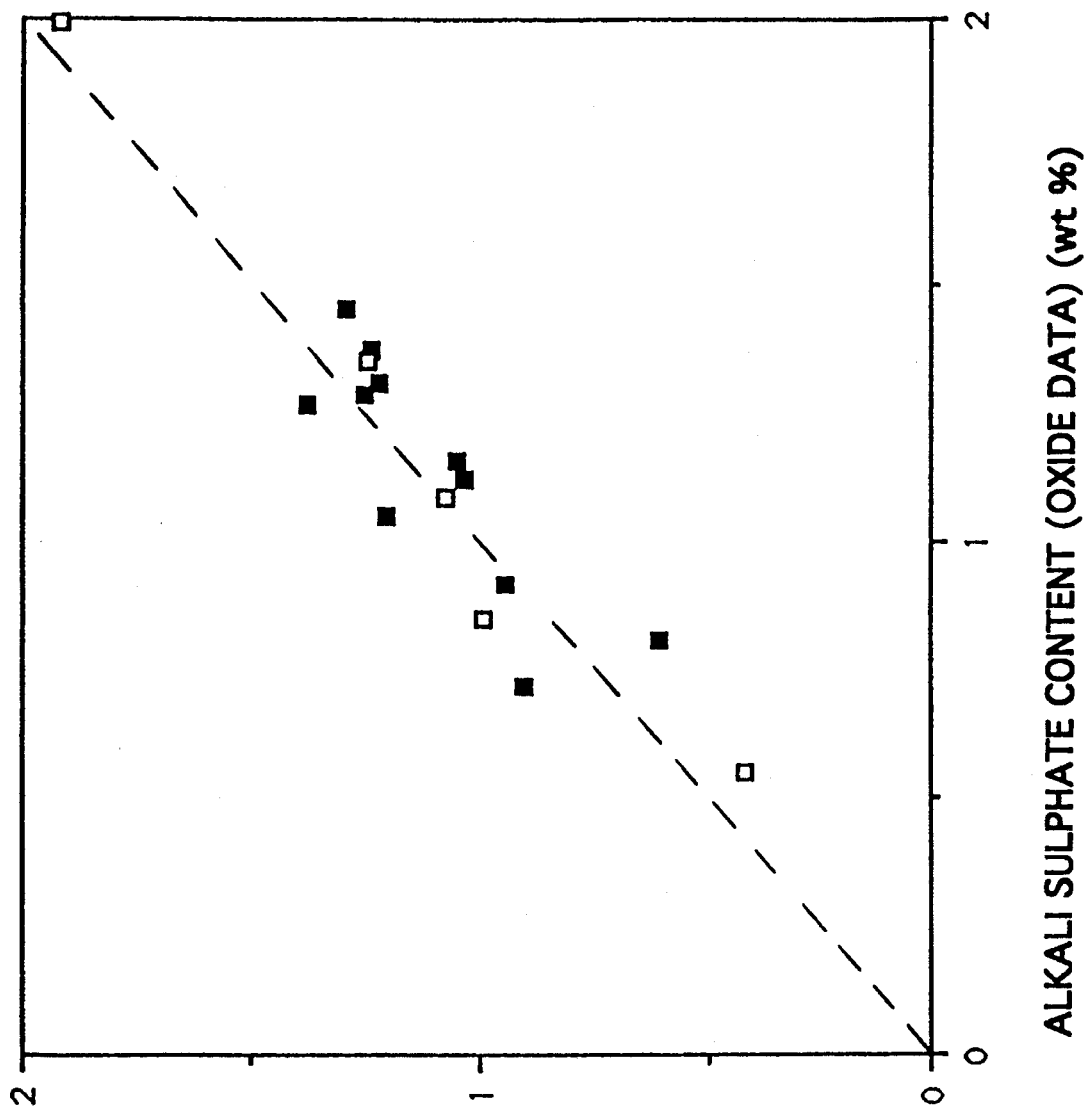
FIG. 11: Prediction of alkali sulphate content from FTIR spectra: validation samples.
Figure 12:
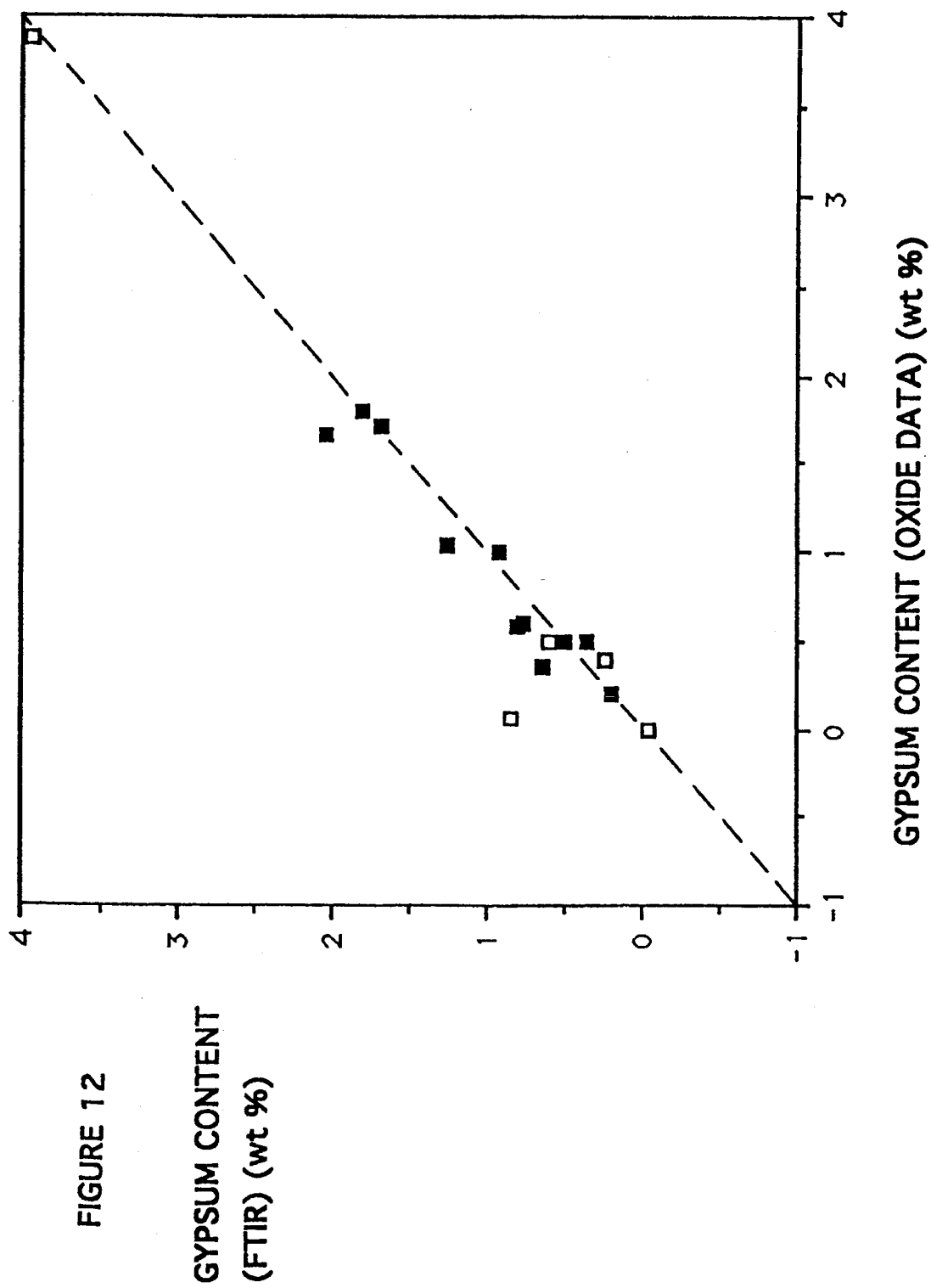
FIG. 12: Prediction of gypsum content from FTIR spectra: validation samples.
Figure 13:
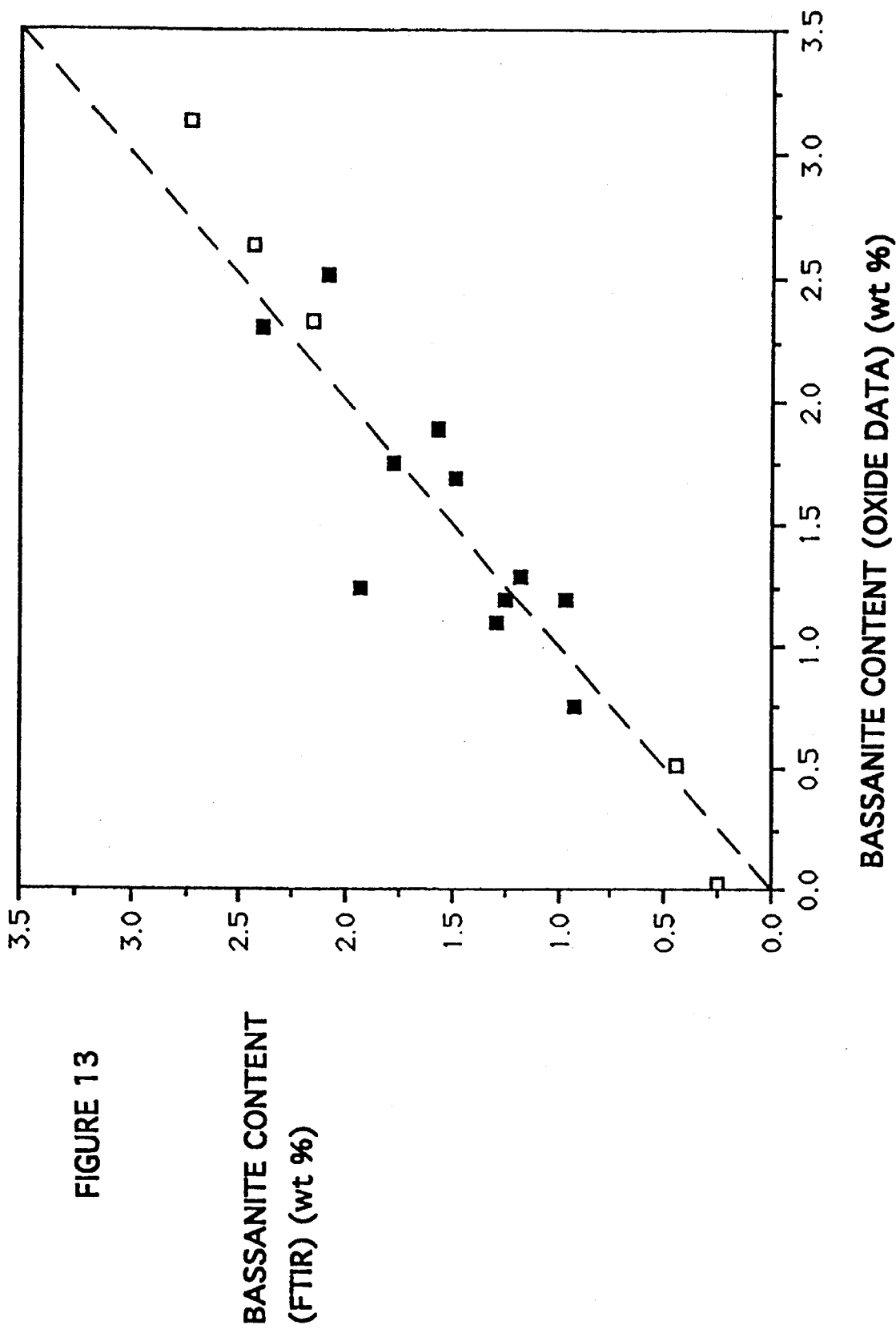
FIG. 13: Prediction of bassanite content from FTIR spectra: validation samples.

Of the total of 35 calibration standards, 15 were chosen as validation samples. The correlation coefficients for each component in the calibration and validation samples of the PLS calibration model are shown in Table 1; the concentration ranges of each component in the 35 calibration standards are also given. Predicted concentrations for the validation samples serve as a preliminary evaluation of the accuracy of the technique. FTIR predictions of Alite, Belite, Aluminate, Ferrite, free lime, alkali sulphate, gypsum and bassanite concentrations in the 15 validation samples are compared to corresponding concentrations calculated from the oxide (Bogue) analyses in FIGS. 7 through to 14. In these figures data from both oilfield cements (□) and construction cements (■) are used. In general, Alite and Belite contents (refer to FIGS. 7 and 8) are predicted within ±5% (in absolute terms) of the values given by the Bogue calculation; this converts to a relative accuracy of ±8–11% for the determination of Alite in the range 45–65 wt. % and ±16–50% for the determination of Belite in the range 10–30 wt. %. The oilfield samples (1) and (2) are "outliers" which deserve special note; whilst the total (Alite+Belite) content of these samples is well predicted by the model (to within ±1% in absolute terms), the individual predictions of Alite and Belite indicate that the samples may have a lower Alite/Belite ratio than is indicated by the Bogue calculation. FIGS. 9 and 10 show the Aluminate and Ferrite predictions for the validation samples; these two components are predicted to within ±1% and ±2% (absolute) of the values given by the Bogue calculation, respectively. FIGS. 9 and 10 also serve to discriminate between the oilfield samples which have high Ferrite and low Aluminate contents relative to the construction samples. FIGS. 11 to 14 show the free lime, alkali sulphate, gypsum and bassanite predictions for the validation samples; these four components are predicted within ±0.2%, ±0.2%, ±0.3% and ±0.3% (absolute) of the values given by the ASTM titration method (free lime) and the oxide data/spectral examination (sulphates). It is notable that the method is also applicable to clinker samples such as the construction clinker (A) shown on FIGS. 11 to 14.

A further validation of the model is given by the predictions obtained for six completely independent oilfield cement samples. The predictions are compared to "actual" data (given by the Bogue calculation, ASTM free lime titration and spectral examination for the sulphates) in Table 2. The Class A cement (sample 6) is well discriminated from the Class G and H cements (samples 1–5) by its relatively high aluminate and low ferrite content. The six cements have widely varying gypsum/bassanite ratios from sample 5 (gyp/bass=3.2) to sample 4 (gyp/bass=0.03); bassanite is formed by the dehydration of gypsum during the cement grinding process.

A wide variety of cement blends are used in the construction and oilfield industries. Silica-cement blends are often used to protect against long term strength retrogression. A particular cement blend containing silica and Class G cement is commonly used for the cementing of geothermal wells which present challenging high temperature conditions. An appropriate PLS calibration model was designed for the quantification of the silica and cement phase components of the silica-cement blend. The manufacturer of the silica-cement blend uses a silica/cement ratio of 0.4 (by weight); this converts to a silica content in the blend of 28.6% by weight. The phase analysis of the cement blend, as predicted from its FTIR spectrum using the appropriate PLS model, is given in Table 3; the spectral data indicates that the blend has 32.7 wt. % silica which is in good agreement with the manufacturer's specification. The phase analysis of the blend may be used to obtain a phase analysis of the cement component; such data is also given in Table 3.

TABLE 1

Calibration and validation correlation coefficients for each component in PLS model (Example 1)

| | Calibration coefficient | Validation coefficient | Concentration range (wt %) |
|---|---|---|---|
| Alite | 0.828 | 0.846 | 19.92–71.77 |
| Belite | 0.767 | 0.788 | 1.63–48.20 |
| Aluminate | 0.990 | 0.964 | 0–9.61 |
| Ferrite | 0.982 | 0.968 | 4.9–20.46 |
| Free lime | 0.989 | 0.967 | 0–3.92 |
| Alkali sulphate | 0.953 | 0.892 | 0.5–1.87 |
| Gypsum | 0.957 | 0.961 | 0–3.87 |
| Bassanite | 0.897 | 0.941 | 0.02–3.13 |

TABLE 2

Predictions of phase composition of six independent oilfield cements (Example 1)

| COMPONENT | SAMPLE | CEMENT SAMPLE NO.* | | | | | |
|---|---|---|---|---|---|---|---|
| | | 1 | 2 | 3 | 4 | 5 | 6 |
| Alite | Actual | 58.2 | 38.0 | 50.2 | 56.7 | 58.1 | 48.9 |
| | FTIR | 55.0 | 41.1 | 49.1 | 53.1 | 52.6 | 48.5 |
| Belite | Actual | 16.4 | 36.4 | 23.1 | 14.2 | 18.2 | 25.3 |
| | FTIR | 15.6 | 36.5 | 21.8 | 20.2 | 20.6 | 30.9 |
| Aluminate | Actual | 0 | 1.6 | 1.5 | 2.4 | 0 | 7.3 |
| | FTIR | 0.3 | 0.7 | 1.4 | 1.8 | −0.9 | 4.4 |
| Ferrite | Actual | 15.2 | 14.6 | 14.7 | 13.9 | 14.5 | 7.8 |
| | FTIR | 15.6 | 15.6 | 13.1 | 9.3 | 14.8 | 8.7 |
| Free lime | Actual | 1.0 | 2.7 | 1.9 | 2.0 | 1.7 | 2.2 |
| | FTIR | 1.3 | 2.8 | 1.9 | 2.2 | 2.0 | 2.0 |
| Alkali sulphate | Actual | 1.1 | 1.2 | 0.8 | 1.0 | 0.6 | 1.1 |
| | FTIR | 1.5 | 1.0 | 0.5 | 0.4 | 0.7 | 1.2 |
| Gypsum | Actual | 1.8 | 1.6 | 1.0 | 0.1 | 3.2 | 2.9 |
| | FTIR | 1.9 | 2.2 | 1.2 | 0.2 | 3.7 | 4.0 |
| Bassanite | Actual | 1.5 | 0.5 | 1.9 | 3.0 | 1.1 | 1.0 |
| | FTIR | 1.7 | 0.7 | 2.2 | 3.2 | 1.0 | 0.8 |

*Samples 1–4 are Class 'G'; samples 5 and 7 are Class 'H' and 'A' respectively.

TABLE 3

Phase analysis of silica-cement blend (Example 2)

| | | Phase analysis of the cement blend | Phase analysis of cement component given silica/cement ratio of blend sample |
|---|---|---|---|
| Silica | Actual* | 28.6 | — |

TABLE 3-continued

Phase analysis of silica-cement blend (Example 2)

|  |  | Phase analysis of the cement blend | Phase analysis of cement component given silica/cement ratio of blend sample |
|---|---|---|---|
| Alite | FTIR | 32.7 | — |
|  | Actual† | 35.0 | 49 |
| Belite | FTIR | 41.4 | 62 |
|  | Actual† | 17.1 | 24 |
| Aluminate | FTIR | 23.4 | 35 |
|  | Actual† | 1.1 | 1.5 |
| Ferrite | FTIR | 0.9 | 1.3 |
|  | Actual† | 10.6 | 14.8 |
| Alkali sulphate | FTIR | 9.0 | 13.4 |
|  | Actual* | — | — |
| Gypsum | FTIR | 0 | 0 |
|  | Actual* | — | — |
| Bassanite | FTIR | 1.4 | 2.1 |
|  | Actual* | — | — |
|  | FTIR | 0.6 | 0.9 |

*from manufacturers specifications (silica/cement ratio = 0.4)
†Bogue oxide analysis of cement component
˙data not available

We claim:

1. A method of analyzing the phase composition of a cement, the method comprising the steps of a) preparing a calibration model by relating measured infrared spectra of samples to the phase composition thereof so as to relate differences between spectra of the samples to differences in phase composition of the samples; and b) obtaining the infrared spectrum of a sample of unknown phase composition and comparing the spectrum with the calibration model so as to determine the phase composition of the sample, characterized in that the model relates the infrared spectra to the composition with regard to more than one phase of the samples, and the composition of the sample of unknown phase composition is determined with regard to said more than one phase quantitatively and simultaneously from the infrared spectrum.

2. The method as claimed in claim 1, wherein the calibration model is derived from a number of calibration standards the total number of which is at least three times the number of analyte components.

3. The method as claimed in claim 1, wherein the phase composition is determined in terms of Bogue phases or modified Bogue phases.

4. The method as claimed in claim 1, wherein the samples comprise dry powders.

5. The method as claimed in claim 1, wherein the infrared spectra are obtained by a diffuse reflectance technique.

6. The method as claimed in claim 1, wherein the different forms of calcium sulphate are determined for the model and analyzed for the unknown sample, and wherein the calcium sulphate composition of the samples used for the calibration model is determined from the infrared spectra of the samples.

7. The method as claimed in claim 1, wherein the free lime content or calcium hydroxide and calcium carbonate content of the sample is included in the calibration model, and is determined by titration.

8. The method as claimed in claim 1, wherein the alkali sulphate content of the sample is included in the calibration model.

9. The method as claimed in claim 1, wherein the clinker phase composition of the samples used for the calibration model is determined by oxide analysis, and the oxide analysis is performed by XRF and/or ICP.

* * * * *